(12) United States Patent
Hernandez Chafes

(10) Patent No.: US 8,876,767 B2
(45) Date of Patent: Nov. 4, 2014

(54) EAR IRRIGATION DEVICE

(76) Inventor: Federico Javier Hernandez Chafes, Barcelona (ES)

(*) Notice: Subject to any disclaimer, the term of this patent is extended or adjusted under 35 U.S.C. 154(b) by 49 days.

(21) Appl. No.: 13/811,780

(22) PCT Filed: Jul. 19, 2011

(86) PCT No.: PCT/IB2011/001673
§ 371 (c)(1),
(2), (4) Date: Jan. 25, 2013

(87) PCT Pub. No.: WO2012/014035
PCT Pub. Date: Feb. 2, 2012

(65) Prior Publication Data
US 2013/0123701 A1    May 16, 2013

(30) Foreign Application Priority Data
Jul. 26, 2010 (EP) .................................. 10380098

(51) Int. Cl.
*A61M 31/00* (2006.01)
*A61M 3/02* (2006.01)

(52) U.S. Cl.
CPC ............ *A61M 3/02* (2013.01); *A61M 3/0262* (2013.01); *A61M 2210/0662* (2013.01)
USPC ........................................ 604/135; 604/514

(58) Field of Classification Search
CPC ........... A61M 5/20; A61M 5/30; A61M 5/19; A61M 5/3007; A61M 5/3137
USPC ............................. 604/134–135, 156, 514, 71
See application file for complete search history.

(56) References Cited

U.S. PATENT DOCUMENTS
2002/0151839 A1* 10/2002 Landau ........................... 604/68

FOREIGN PATENT DOCUMENTS
DE          10202367 A1    9/2003
ES           1067832 U     7/2008
WO        WO 99/26684 A1   6/1999
WO       WO 2012/014035 A1 2/2012

* cited by examiner

*Primary Examiner* — Nicholas Lucchesi
*Assistant Examiner* — Melissa A Snyder
(74) *Attorney, Agent, or Firm* — Hess Patent Law Firm LLC; Robert J. Hess

(57) ABSTRACT

The ear irrigation device for the removal of earwax integrates a fluid injector assembly with a fluid container (2) which is loaded and discharged by means of a guided rod (3) and plunger (4) assembly with bidirectional linear sliding through its inside, arranged in the container (2), which it divides into a front chamber (2*a*) and a rear chamber (2*b*), an actuating element (5) to move the rod-plunger assembly (3, 4) to said retracted position, a retaining element (13) to retain it, and a nozzle portion (6) for discharging by ejection the fluid of the front chamber (2*a*) of the container (2) having been provided. A handgrip (7) with a trigger (8) controls the retaining element (13) to release the rod-plunger assembly (3, 4) and allow it to move towards said extended position. The rod (3) of the plunger (4) is hollow and houses a fixed axial guide element (10) and a spring (12) coaxial to the axial element (10).

14 Claims, 4 Drawing Sheets

EAR IRRIGATION DEVICE

TECHNICAL FIELD

The present invention relates to an ear irrigation device for the removal of earwax by means of entraining it with a fluid injected under pressure into the ear by the push of a movable plunger, and more particularly to a device with a stable guiding configuration for said plunger.

PRIOR STATE OF THE ART

Currently, within the mechanisms for the mechanical extraction of earwax plugs, the extraction by means of the entrainment with pressurized water injected into the ear canal by means of an injector utensil is the most used one.

Generally, said injector utensil simply consists of a syringe, but there are proposals which describe more sophisticated injector mechanisms, as is the case of the one described by utility model ES 1 067 832 U, where the injector mechanism consists of a gun formed by a body comprising a handgrip and acting as a support of a water container, inside which there moves linearly a plunger fixed to a first end of a rod, a second end of which comes out to the exterior of the container through a through hole defined in a rear wall thereof, and is attached to said grip element so that a user can pull it to move it outwards and thus move the plunger to a retracted position, suctioning water into the container through a nozzle like in a conventional syringe.

In said retracted position, the plunger is retained and is moved to an extended position to push the liquid contained in the container for the purpose of ejecting it through the nozzle, by means of the force exerted by a motor operated by a trigger arranged in the handgrip.

Although the plunger-rod assembly is moved through the inside of the container in a manner guided by two regions, one achieved by the adaptation and sliding of its outer perimeter with respect to the inner perimeter of the container, and the other one achieved by the adaptation and sliding of the outer perimeter of the rod with respect to the perimetric wall of the through hole defined in the rear wall of the container, such guiding of the plunger-rod assembly is improvable, particularly with regard to the stability that it provides.

DISCLOSURE OF THE INVENTION

The present invention provides an alternative to the state of the art in the form of an injector utensil including guiding configurations which provide greater stability for the movement of the plunger-rod assembly included therein.

For such purpose, the present invention relates to an ear irrigation device for the removal of earwax, which integrates in a known manner:
 a fluid injector assembly formed by
  a body defining
   a container for the mentioned fluid which is loaded into the container and discharged therefrom by means of
   a rod and plunger assembly arranged with hermetic sealing in said container, which it divides into a front chamber for the fluid and a rear chamber, and with the possibility of bidirectional linear sliding through its inside between a retracted position and an extended position, and vice versa,
   an actuating element to move said rod-plunger assembly to said retracted position, and
   a retaining element to retain said rod-plunger assembly in said retracted position, and
  a nozzle portion, through which to discharge, by ejection, the fluid of the front chamber of the container, and
  a handgrip with
   a trigger controlling the mentioned retaining element, to release the rod-plunger assembly retained by the latter and to allow it to move towards said extended position.

The device proposed by the present invention is characterized in that the end of the rod distal from the plunger has attached thereto a part acting as a guide which slides inside the rear chamber of the container.

Unlike the background document mentioned in the previous section, for one embodiment, the device proposed by the present invention does not use a motor for moving the plunger-rod assembly towards the extended position, but rather it uses a spring which is compressed when the plunger-rod assembly is in the retracted position, with a compression force calculated so that, once the rod-plunger assembly is released, it pushes them with a predetermined force to move them to the mentioned extended position such that the fluid is ejected with the desired pressure, suitable for the extraction of the earwax but insufficient for damaging the ear.

BRIEF DESCRIPTION OF THE DRAWINGS

The previous and other advantages will be more fully understood from the following detailed description of several embodiments with reference to the attached drawings, which must be taken in an illustrative and non-limiting manner, in which.

DETAILED DESCRIPTION OF EXEMPLARY EMBODIMENTS

Figure 3:
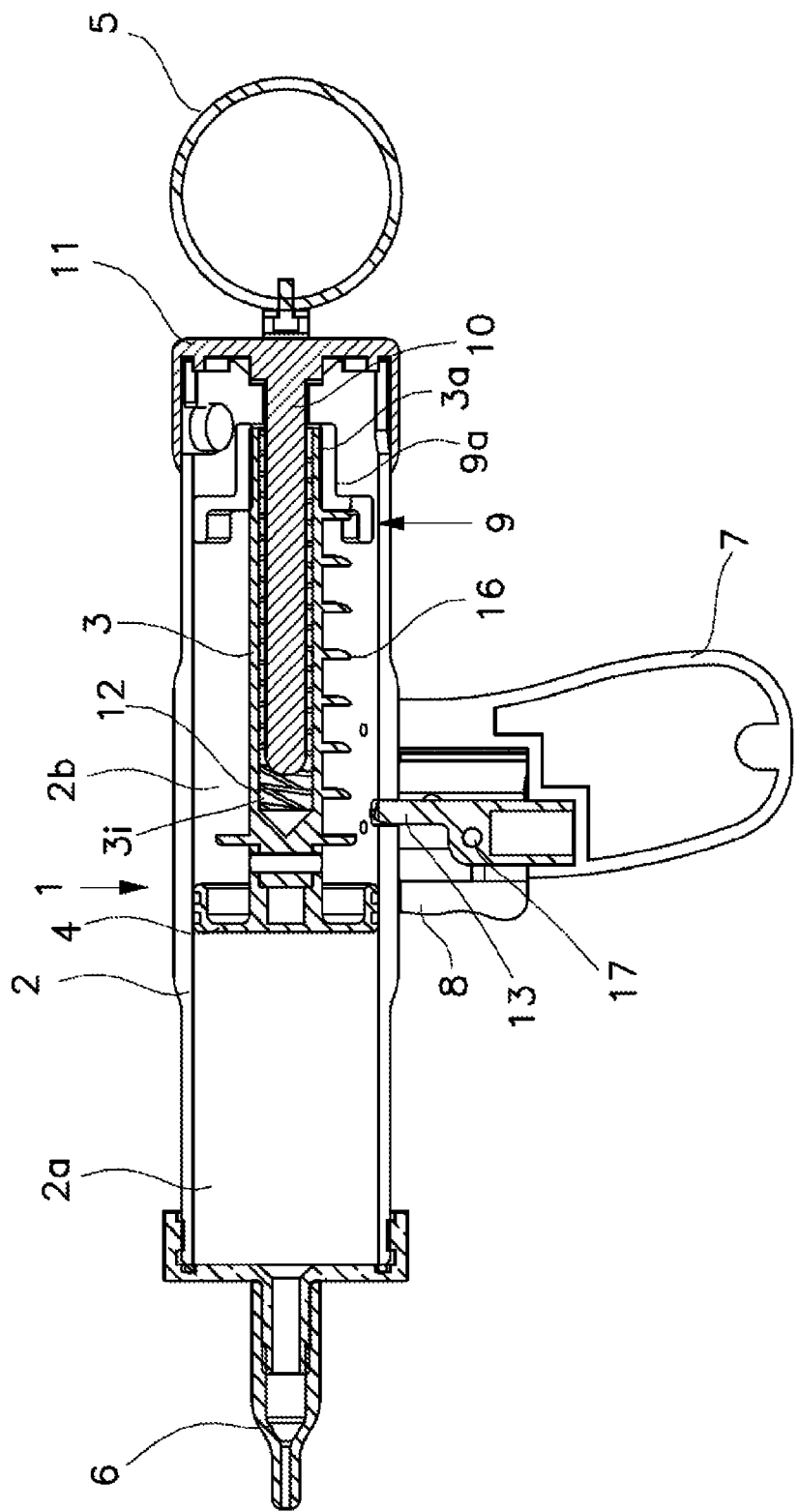
FIG. 3 is a side elevational view of the device of FIG. 1, sectioned through a plane traversing the longitudinal axis of symmetry thereof.

As shown in the attached figures, particularly FIG. 3, the ear irrigation device for the removal of earwax proposed by the present invention integrates:
 a fluid injector assembly formed by
  a body 1 defining
   a container 2 for the mentioned fluid which is loaded into the container 2 and discharged therefrom by means of
   a rod 3 and plunger 4 assembly arranged with hermetic sealing in said container 2, which it divides into a front chamber 2a for the fluid and a rear chamber 2b, and with the possibility of bidirectional linear sliding through its inside between a retracted position and an extended position, and vice versa,
   an actuating element 5 for said rod-plunger assembly 3, 4, to move it to said retracted position, and
   a retaining element 13 for said rod-plunger assembly 3, 4, to retain it in said retracted position, and
  a nozzle portion 6, through which to discharge, by ejection, the fluid of the front chamber 2a of the container 2, and
  a handgrip 7 with
   a trigger 8 controlling the mentioned retaining element 13, to release the rod-plunger assembly 3, 4 retained by the latter and allowing it to move towards said extended position.

Figure 1:
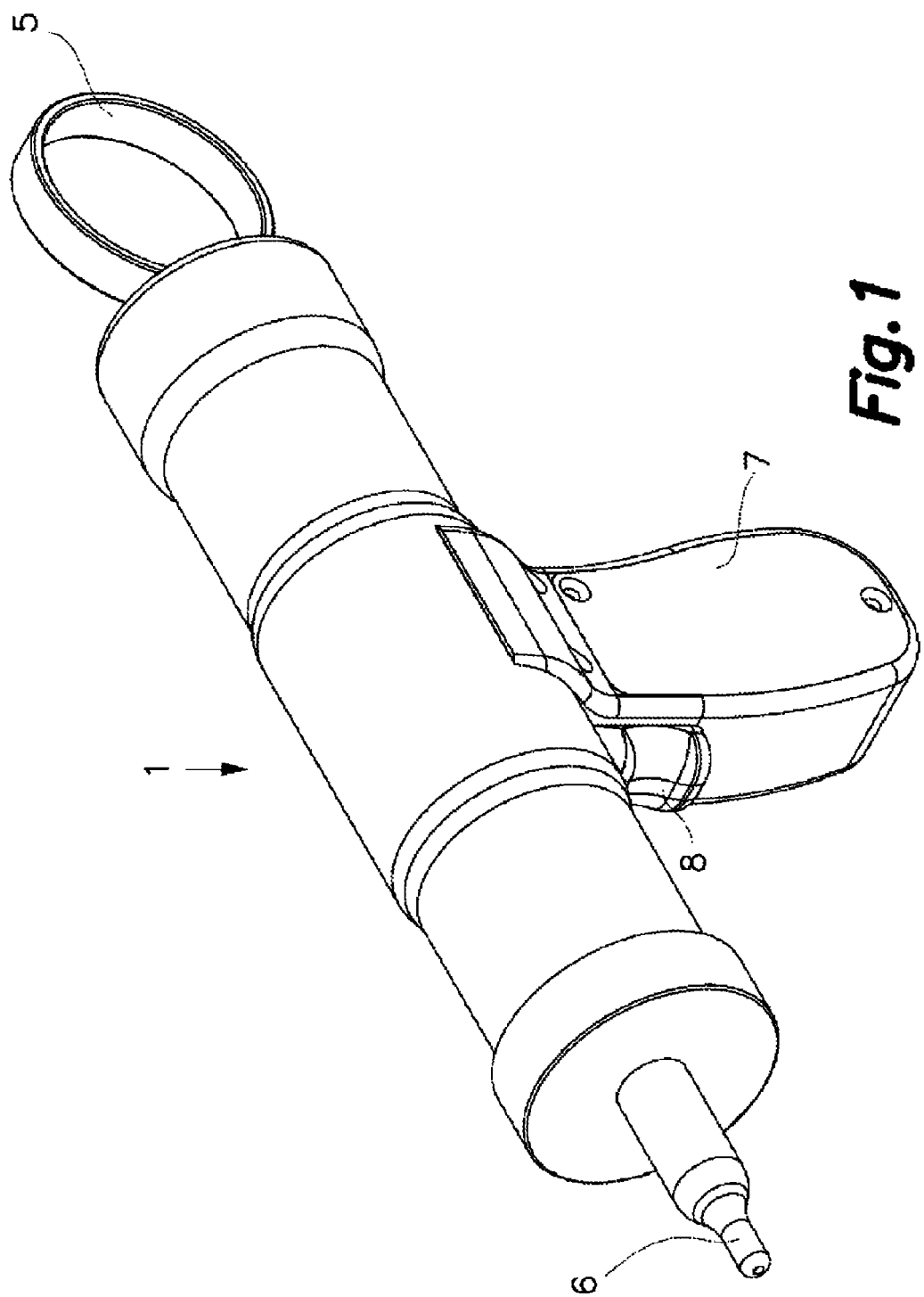
FIG. 1 is a perspective view of the device proposed by the present invention, for one embodiment.
Figure 2:
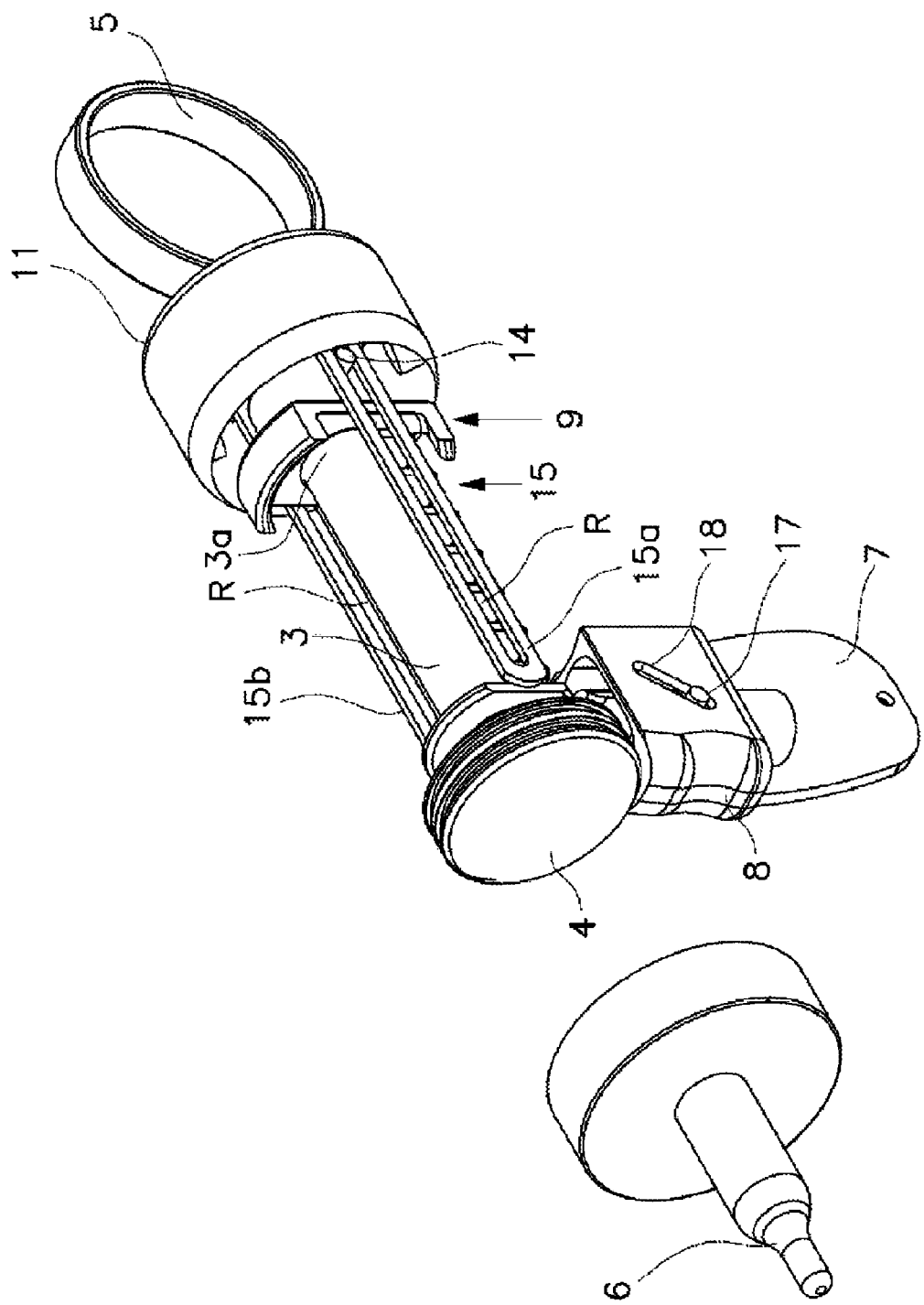
FIG. 2 is a perspective view of part of the device illustrated in FIG. 1, with its inner components exposed.
Figure 4:
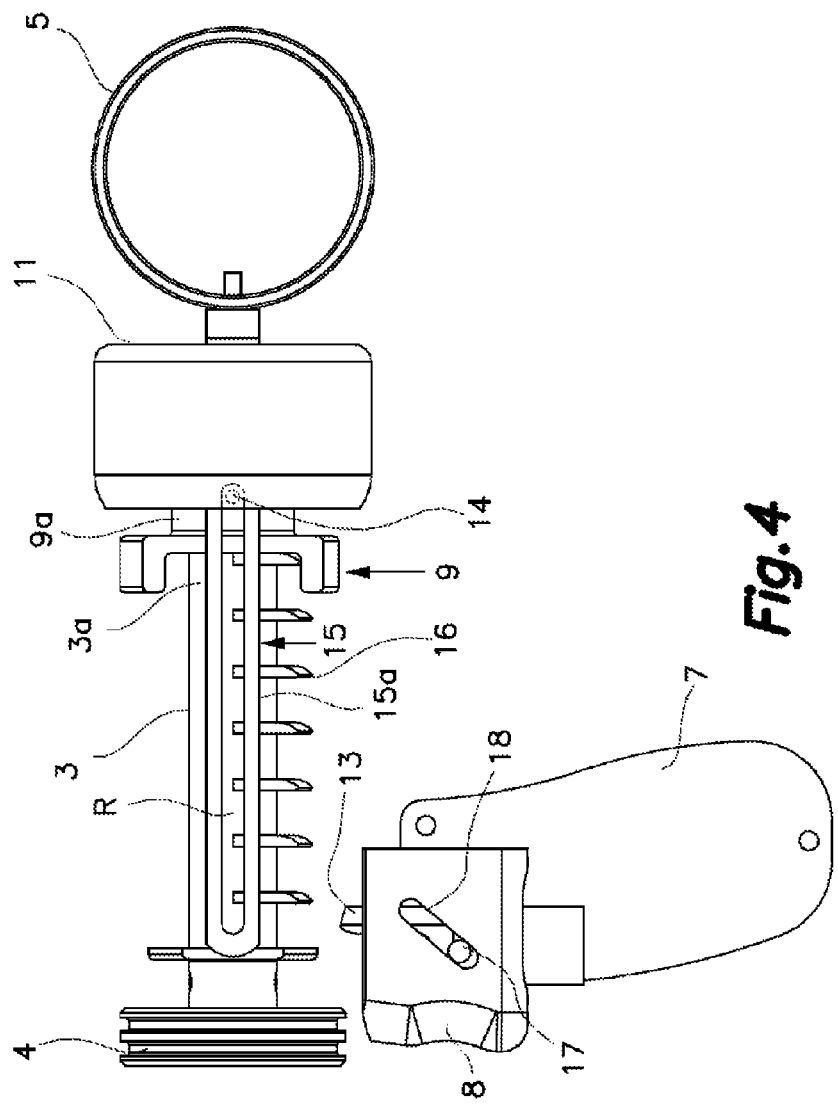
FIG. 4 is a side elevational view showing the elements illustrated by FIG. 2.
Figure 4:
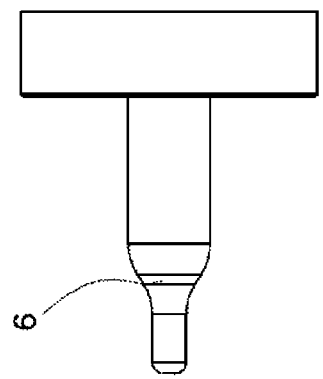

As can be seen in FIGS. 2, 3 and 4, the end 3a of the rod 3 distal from the plunger 4 has attached thereto a part 9 acting as a guide which slides inside the rear chamber 2b of the container 2.

In particular, in FIG. 3 it can be seen how, for the embodiment illustrated therein, the rod 3 of the plunger 4 is hollow and provided for housing, when the rod-plunger assembly 3, 4 moves, a fixed axial guide element 10 starting from an end part 11 for closing the container 2, furthermore integrating a spring 12 coaxial to the mentioned axial element 10 which is likewise received inside the hollow rod 3, which spring 12 extends from the starting area of the axial element 10 to the bottom of the hollow 3i of the rod 3 of the plunger 4, such that it is compressed when the axial element 10 is inserted in the hollow 3i of the rod 3 and provides the actuation force so that the plunger 4, when it is released by means of the mentioned trigger 8, moves towards said extended position to push the fluid of the front chamber 2a of the container 2 and discharge it by ejection through said nozzle portion 6.

The spring 12 is calculated to provide a determined speed of the fluid when exiting the front chamber 2a of the container 2.

For one embodiment, which is not illustrated, the spring 12 comprises the juxtaposition of several spring sectors.

FIGS. 3 and 4 show how the mentioned part 9 acting as a guide has associated therewith a cylindrical protrusion 9a in which pins 14 are locked, which pins extend into grooves R of respective opposing arms 15a, 15b of a U-shaped part 15 (see FIG. 2), which emerges to the exterior of the container 2 and is attached to a pull forming the mentioned actuating element 5, compressing the mentioned spring 12 by the traction of said U-shaped part 15 driving the rod-plunger assembly 3, 4.

FIGS. 3 and 4 show how the hollow rod 3 has in its outer face a plurality of equidistant flanges 16 which can interfere with the retaining element 13, elastically loaded and controlled by the mentioned trigger 8 for the purpose of releasing the mentioned rod 3, from a situation of compression of the spring 12, and with the possibility of stopping the movement in any desired position.

As can be seen in FIG. 3, the trigger 8 comprises a pusher operating against a pin 17 transversely linked to the mentioned retaining element 13, by means of the push by the perimetric wall of oblique elongated openings 18 against the ends of said pin 17 introduced in such openings, such that the movement of the trigger 8 forces the retaining element 13 to move downwards, loading a spring (not illustrated), and its release returns the retaining element 13 to a position of interference with the mentioned flanges 16.

The mentioned U-shaped part and pull 5 are retractable towards the inside of the rear chamber 2b of the container 2 once the plunger 4 has been moved to said retracted position, or loaded position, and retained in said position by the retaining element 13.

It can be seen that for the embodiment illustrated by FIGS. 2, 3 and 4, the part 9 acting as a guide has a span equivalent to the plunger 4.

A person skilled in the art could introduce changes and modifications in the described embodiments without departing from the scope of the invention as it is defined in the attached claims.

The invention claimed is:

1. An ear irrigation device for the removal of earwax, which integrates
a fluid injector assembly formed by
a body defining
a container for fluid which is loaded into the container and discharged therefrom by means of
a rod and plunger assembly arranged with hermetic sealing in said container, so as to divide the container into a front chamber for the fluid and a rear chamber, and enable bidirectional linear sliding of the rod and plunger assembly through an inside of the container between a retracted position and an extended position, and vice versa,
an actuating element to move said rod and plunger assembly to said retracted position,
a retaining element to retain said rod and plunger assembly in said retracted position,
a nozzle portion, through which the fluid of the front chamber of the container is discharged by ejection, and
a handgrip with a trigger controlling at least the retaining element to release the rod and plunger assembly retained by the latter and to allow the rod plunger assembly to move towards said extended position, wherein:
the rod and plunger assembly includes a hollow rod having an end that is distal from said plunger and is attached to a part acting as a guide which slides inside said rear chamber of the container,
the hollow rod of the plunger is hollow and is provided for housing, when the rod and plunger assembly moves, a fixed axial guide element starting from an end part for closing the container, and
a spring is provided coaxial to the fixed axial guide element, said spring being housed inside the hollow rod.

2. The device according to claim 1, wherein the spring extends from the starting area of the axial element to the bottom of the hollow of the hollow rod of the plunger, such that the spring is compressed when the axial element is inserted in the hollow of the hollow rod and provides the actuation force so that the plunger, when the spring is released by means of the trigger, moves towards said extended position to push the fluid of the front chamber of the container and discharge the fluid by ejection through said nozzle portion.

3. The device according to claim 1 or 2, wherein said spring provides a determined speed of the fluid exiting the front chamber of the container.

4. The device according to claim 2, wherein said spring comprises the juxtaposition of several spring sectors.

5. The device according to claim 1, wherein the part acting as a guide has associated therewith a cylindrical protrusion in which pins are locked, the pins extending into grooves of respective opposing arms of a U-shaped part, which emerges to an exterior of the container and is attached to a pull forming the actuating element (5) and compresses the spring by traction of said U-shaped part to drive the rod and plunger assembly.

6. The device according to claim 2, wherein the hollow rod has in an outer face a plurality of flanges which can interfere with said retaining element, which is elastically loaded and controlled by the trigger, for the purpose of releasing the hollow rod from a situation of compression of the spring so as to enable stopping of movement of the rod and plunger assembly in any desired position.

7. The device according to claim 6, wherein said flanges are equidistant.

8. The device according to claim 6 or 7, wherein the trigger comprises a pusher operating against a pin transversely linked to the retaining element, by means of the push by the perimetric wall of oblique elongated openings against the ends of said pin introduced in such openings, such that the movement of the trigger forces the retaining element to move downwards loading a spring, and its release returns the retaining element to a position of interference with the flanges.

9. The device according to claim 5, wherein the U-shaped part and pull are retractable towards the inside of the rear chamber of the container once the plunger has been moved to said retracted position, or loaded position, and retained in said position by the retaining element.

10. The device according to claim 1, wherein said part acting as a guide has a span equivalent to the plunger.

11. The device according to claim 3, wherein said spring comprises the juxtaposition of several spring sectors.

12. An ear irrigation device for the removal of earwax, which integrates a fluid injector assembly formed by:
   a body defining
   a container for fluid which is loaded into the container and discharged therefrom by means of
   a rod and plunger assembly arranged with hermetic sealing in said container to divide the container into a front chamber for the fluid and a rear chamber so as to enable bidirectional linear sliding of the rod and plunger assembly through an inside of the container between a retracted position and an extended position, and vice versa,
   an actuating element to move said hollow rod and plunger assembly to said retracted position,
   a retaining element to retain said hollow rod and plunger assembly in said retracted position,
   a nozzle portion, through which the fluid of the front chamber of the container is discharged by ejection, and
   a handgrip with a trigger controlling at least the retaining element to release the hollow rod and plunger assembly retained by the latter and to allow the rod and plunger assembly to move towards said extended position, wherein:
   the rod and plunger assembly includes a hollow rod with an end that is distal from said plunger and attached to a part acting as a guide that slides inside said rear chamber of the container,
   the hollow rod of the plunger is hollow and is provided for housing, when the hollow rod and plunger assembly moves, a fixed axial guide element starting from an end part for closing the container,
   a spring is provided coaxial to the fixed axial guide element, said spring being housed inside the hollow rod, and
   the part acting as a guide has associated therewith a cylindrical protrusion in which pins are locked, the pins extending into grooves of respective opposing arms of a U-shaped part, which emerges to an exterior of the container and is attached to a pull forming the actuating element so as to compress the spring by traction of said U-shaped part to drive the hollow rod and plunger assembly.

13. The device according to claim 12, wherein the U-shaped part and pull are retractable towards the inside of the rear chamber of the container once the plunger has been moved to said retracted position, or loaded position, and retained in said position by the retaining element.

14. An ear irrigation device for the removal of earwax, which integrates a fluid injector assembly formed by:
   a body defining
   a container for the mentioned fluid which is loaded into the container and discharged therefrom by means of
   a rod and plunger assembly arranged with hermetic sealing in said container to divide the container into a front chamber for the fluid and a rear chamber so as to enable bidirectional linear sliding of the rod and plunger assembly through an inside of the container between a retracted position and an extended position, and vice versa,
   an actuating element to move said rod and plunger assembly to said retracted position,
   a retaining element to retain said rod and plunger assembly in said retracted position,
   a nozzle portion, through which the fluid of the front chamber of the container is discharged by ejection, and
   a handgrip with a trigger controlling at least the retaining element to release the rod and plunger assembly retained by the latter so as to allow the rod and plunger assembly to move towards said extended position, wherein:
   the rod and plunger assembly includes a hollow rod that has an end that is distal from said plunger and attached to a part acting as a guide that slides inside said rear chamber of the container,
   the hollow rod of the plunger is hollow and is provided for housing, when the rod-plunger assembly moves, a fixed axial guide element starting from an end part for closing the container,
   a spring is provided coaxial to the fixed axial guide element, said spring being housed inside the hollow rod;
   the part acting as a guide has associated therewith a cylindrical protrusion in which pins are locked, the pins extending into grooves of respective opposing arms of a U-shaped part, which emerges to an exterior of the container and is attached to a pull forming the actuating element and compresses the spring by traction of said U-shaped part to drive the rod-plunger assembly, and
   the U-shaped part and pull are retractable towards an inside of the rear chamber of the container once the plunger has been moved to said retracted position, or loaded position, and retained in said position by the retaining element.

* * * * *